United States Patent [19]

Barra et al.

[11] 4,096,252

[45] Jun. 20, 1978

[54] 4-TRIFLUOROMETHYLBENZOIC ACID DERIVATIVES AS THROMBOEMBOLIC AGENTS

[75] Inventors: Emilia Francia Barra; Antonio Carmelo Marin Moga, both of Barcelona, Spain

[73] Assignee: J. Uriach & Cia S.A., Barcelona, Spain

[21] Appl. No.: 694,523

[22] Filed: Jun. 10, 1976

[51] Int. Cl.$^2$ .............................................. A61K 31/60
[52] U.S. Cl. .............................. 424/230; 260/521 H; 560/143
[58] Field of Search ...................... 260/479 R; 424/230

[56] References Cited

U.S. PATENT DOCUMENTS 3,019,253   1/1962   Hauptschein ................... 260/479 R

*Primary Examiner*—Alan L. Rotman
*Assistant Examiner*—Jane T. Fan
*Attorney, Agent, or Firm*—Michael J. Striker

[57] ABSTRACT

2-OR-4-trifluoromethylbenzoic acid wherein R is H or acyl.

The compounds are useful in the treatment of pathological cardiovascular conditions, particularly in the prophylaxis of the thromboembolic diseases.

The compounds are made by reacting m-trifluoromethyl phenol with potassium carbonate and carbon dioxide at an elevated temperature and pressure and, if desired, acetylating the 2-OH compound thus obtained or reacting it with a phosphonating agent.

The invention also embraces pharmaceutical compositions in which the compounds constitute the effective agent and a method of treatment.

2 Claims, 2 Drawing Figures

TYPICAL CURVE OF HUMAN PLATELET AGGREGATION INDUCED BY COLLAGEN. THE SIGNIFICANCE OF THE PARAMETERS EMPLOYED IN TABLE IV (x, y AND DELAY) IS INDICATED

TYPICAL HUMAN THROMBOELASTOGRAMS OF RICH PLATELET PLASMA (a), BLOOD (b) AND POOR PLATELET PLASMA (c). THE VALUES r AND k (IN PARAMETER 15 OF TABLE V) CORRESPOND TO BLOOD (b) THEIR SIGNIFICANCE APPEARS FROM THE FIGURE

4-TRIFLUOROMETHYLBENZOIC ACID DERIVATIVES AS THROMBOEMBOLIC AGENTS

BACKGROUND OF THE INVENTION

The present invention relates to 2-hydroxy-4-trifluoromethylbenzoic acid, 2-acyl derivatives thereof, particularly acetic and orthophosphoric esters, and pharmaceutically acceptable salts thereof and its use in treating cardiovascular conditions related to thromboembolic diseases.

It is known that the medical problem of thrombosis encompasses three distinct physiological phenomena: platelet aggregation, coagulation and fibrinolysis. Therefore, drugs capable of having an action upon one or more of these phenomena are useful from a prophylactic or a therapeutic standpoint in various clinical situations, related to thromboembolic diseases, see POOLE, JCF, J. Atheroscl. Res. 1: 251, 1961, and FLEMING, JS, Antithromboembotic agents, in Heinzelman RV, Annual Reports in Medicinal Chemistry. Vol. 9, Academic Press, New York, 1974, p. 75.

The claimed compounds have been found to have an effect on the mentioned physiological processes, especially platelet aggregation and certain factors concerning the blood coagulation system and fibrinolysis. This fact makes them useful therapeutical tools for the treatment of thromboembolic diseases.

SUMMARY OF THE INVENTION

The compounds of the invention have the following chemical structure:

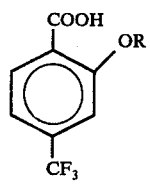

where R is hydrogen or an acyl radical, particularly acetyl or phosphono.

The invention also embraces processes for the preparation of the compounds, which are as follows:

2-hydroxy-4-trifluoromethylbenzoic acid, corresponding to the following structural formula:

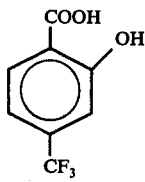

may be prepared from the commercially available m-trifluoromethylphenol, having the formula:

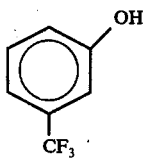

by the conventional Kolbe-Schmitt reaction, in which the introduction of the carboxy group in the above mentioned phenol is carried out by heating it with potassium carbonate in the presence of carbon dioxide under pressure.

For the preparation of the acetyl derivative, having the formula:

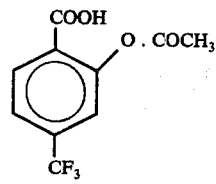

the previously prepared 2-hydroxy-4-trifluoromethylbenzoic acid is treated with an acetylating agent and in case of the phosphonoxy derivative with a phosphonating agent. Suitable acetylating agents are acetic anhydride ($(CH_3—CO)_2O$), acetyl chloride ($CH_3COCl$) or the highly unsaturated, reactive ketene ($CH_2=C=O$). The reaction is carried out in different ways according to the nature of the acetylating agent employed. Thus, when acetic anhydride is used, 2-hydroxy-4-trifluoromethylbenzoic acid is directly dissolved in the reagent and a catalyst may be added. However, the acetylation with acetyl chloride proceeds better in the presence of an inert solvent and a suitable basic compound for combining with the hydrochloric acid produced as by-product. The acetylation with ketene is carried out by introducing this reagent into a solution of 2-hydroxy-4-trifluoromethylbenzoic acid in an inert solvent.

DESCRIPTION OF SPECIFIC EMBODIMENTS

Figure 1:
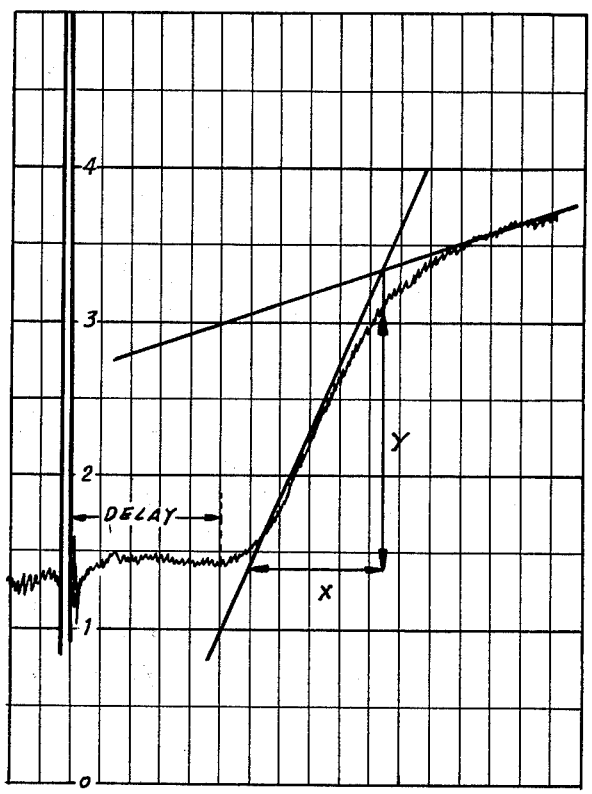
FIG. 1 shows a typical curve of human platelet aggregation induced by collagen. The significance of the parameters employed in Table IV ($x$, $y$ and delay) is indicated.

The invention is further explained by reference to the following examples, without intention to limit it thereby.

EXAMPLE 1

Preparation of 2-hydroxy-4-trifluoromethylbenzoic acid 162.11 g (1 mole) of the commercially available m-trifluoromethylphenol and 414.60 g (3 moles) of anhydrous potassium carbonate are intimately mixed and placed in a high pressure device. Carbon dioxide is introduced in the apparatus at a pressure of 40 atm and this pressure is maintained while the temperature is slowly raised up to 190° C during the course of a week. When this reaction time has elapsed, the mixture is allowed to cool to room temperature and the pressure released. The solid mass obtained is dissolved in 3000 ml of hot water and the strongly alkaline solution, after cooling, is extracted twice with 250 ml ethyl ether portions in order to remove traces of unreacted product.

The aqueous layer is then carefully acidified with hydrochloric or sulphuric acid until a distinctly acid pH value is obtained, which causes the insoluble 2-hydroxy- 4-trifluoromethylbenzoic acid to precipitate. The solid is filtered off, thoroughly washed with cold water and finally recrystallized twice from a mixture of ethanol and water (1:1). Thus, 134 g (65% yield) of a white crystalline powder, m.p. 180°–181° C are obtained.

Analysis: Calculated for $C_8H_5O_3F_3$: 46.62% C; 2.45% H; 23.29% O; 27.65% F. Found: 46.51 – 46.70% C; 2.43 – 2.45% H; 23.34 – 23.12% O; 27.41 – 27.53% F.

Equivalent weight determined by titration with NaOH: 206.27 – 206.18 g/eq (theoretical 206.12 g/eq).

EXAMPLE 2

Preparation of 2-acetoxy-4-trifluoromethylbenzoic acid with acetic anhydride 20.6 g (0.1 mole) of 2-hydroxy-4-trifluoromethylbenzoic acid obtained according to the method described in Example 1, 70 ml of acetic anhydride and 15 drops of concentrated sulphuric acid are heated at 50°–60° C with stirring during a period of 30 minutes. The reaction mixture is cooled to room temperature and the 2-acetoxy-4-trifluoromethylbenzoic acid is precipitated by addition with stirring of 150 ml of cold water, filtered off, washed with water and dried at a low temperature.

The product is recrystallized twice from a mixture of petroleum ether and ether. 17.4 g (70% yield) of a very pure white crystalline solid, m.p. 120°–122° C (upon slow heating) or 110°–112° C (upon quick heating), are obtained.

Analysis: Calculated for $C_{10}H_7O_4F_3$: 48.40% C; 2.84% H; 25.79% O; 22.97% F. Found: 48.23 – 48.30% C; 2.90 – 2.78% H; 25.70 – 25.96% O; 23.07 – 23.10% F.

Equivalent weight determined by titration with NaOH: 246.79 – 247.90 g/eq (theoretical: 248.16 g/eq)

A qualitative assay for free phenolic groups is negative.

EXAMPLE 3

Preparation of 2-acetoxy-4-trifluoromethylbenzoic acid with acetyl chloride 20.6 g (0.1 mole) of 2-hydroxy-4-trifluoromethylbenzoic acid obtained according to the method described in Example 1 and 12.1 g (0.1 moles) of sym-collidine are dissolved in 300 ml of anhydrous ether. The solution is vigorously stirred and 8.65 g (0.11 mole) of acetyl chloride are slowly added dropwise. Heat is evolved causing the reaction mixture to heat up; therefore, a reflux condenser must be used. The collidine hydrochloride formed as a by-product of the reaction then precipitates in the form of a white solid. After cooling, the collidine hydrochloride is filtered off and the filtrate is washed in a separating funnel with 1N hydrochloric acid and then with water, dried with anhydrous sodium sulphate and the solvent removed in vacuo at room temperature. The residue is crude 2-acetoxy-4-trifluoromethylbenzoic acid, which is further purified by two recrystallizations from a mixture of petroleum ether and ether. Thus, 16.6 g (67% yield) of a pure white crystalline solid, m.p. 119°–121° C (upon slow heating) or 110°–113° C (upon quick heating), are obtained.

Analysis: Calculated for $C_{10}H_7O_4F_3$: 48.40% C; 2.84% H; 25.79% O; 22.97% F. Found: 48.47 – 48.21% C; 2.70 – 2.96% H; 25.63 – 25.92% O; 22.81 – 22.87% F.

Equivalent weight determined by titration with NaOH: 247.28 – 247.02 g/eq (theoretical 248.16 g/eq)

A qualitative assay for free phenolic groups is negative.

Treatment of the precipitate of collidine hydrochloride with concentrated aqueous NaOH and subsequent extraction with ether and purification by distillation, affords a high yield recovery of sufficiently pure sym-collidine, which can be used in another run.

EXAMPLE 4

Preparation of 2-acetoxy-4-trifluoromethylbenzoic acid with ketene

The highly unsaturated, reactive ketene ($CH_2=C=O$) is capable of reacting with the active hydrogen of the free phenolic group of 2-hydroxy-4-trifluoromethylbenzoic acid, yielding an acetyl derivative, the carboxy group of which has simultaneously formed a mixed anhydride, as shown by the following structure:

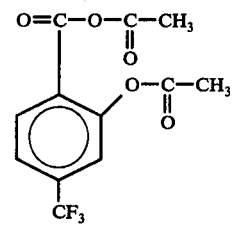

However, under suitable operating conditions, the free acid can be directly recovered by hydrolytic cleavage from the 2-acetoxy-4-trifluoromethylbenzoic acetic anhydride formed in the first step of the reaction.

In view of this course of the reaction in minimum of 2 moles of ketene per mole of product to be acetylated must be employed and a sufficient amount of water must be used to cause the hydrolysis of the mixed anhydride.

The ketene necessary for the reaction must have been freshly prepared. It can be obtained by cracking acetone at 650°–750° C in a conventional apparatus.

More specifically, 20.6 g (0.1 mole) of 2-hydroxy-4-trifluoromethylbenzoic acid are dissolved in 100 ml of anhydrous acetone and 8.2 g (0.22 moles) of ketene vapour from the generator are slowly bubbled without heating through the solution. Then 150 ml of water are added to the reaction mixture and the resulting cloudy solution is allowed to stand overnight at room temperature. Precipitation of highly pure 2-acetoxy-4-trifluoromethylbenzoic acid occurs, which is removed by filtration. Thus 11.0 g (45% yield) of a white crystalline powder, that does not need further purification, are obtained.

An additional amount of less pure product can be recovered by evaporating at room temperature most of the acetone from the mother liquor. This product is purified by recrystallization from a mixture of petroleum ether-ether. 7.0 g (28% yield) of a white crystalline powder are obtained.

The total yield of the operation then is 73%, the analysis of both fractions being satisfactory and the values obtained being similar to those indicated in Examples 2 and 3.

EXAMPLE 5

Preparation of 2-phosphonoxy-4-trifluoromethylbenzoic acid

This reaction is carried out in an analogous manner to that outlined in our copending U.S. application for the preparation of 2-phosphonoxy benzoic acid. Similar theoretical considerations are applicable here, but different experimental conditions must be observed according to the specific physico-chemical properties of the starting and final products.

52.5 g (0.25 mole) of 2-hydroxy-4-trifluoromethyl-benzoic acid are intimately mixed with 52.1 g (0.25 mole) of pure phosphorus pentachloride. Heat is evolved and the mixture, while adequately protected against humidity, is allowed to react. When the mixture begins to liquify, vigorous stirring is started and the temperature is maintained at 60°-65° C during half an hour by means of external heating. After this time has elapsed, the reaction mixture is rapidly cooled in an ice-bath and then dissolved in 200 ml of anhydrous acetone and benzene (1:2). 13.5 ml (0.75 mole) of water are slowly added with a whirling action followed by additional 300 ml of dry benzene. The mixture is allowed to stand overnight at room temperature in order to complete precipitation of the 2-phosphonoxy-4-trifluoromethylbenzoic acid and the product is filtered off, washed with dry benzene and dried in vacuo over an alkaline dehydrating agent to remove the contaminant hydrochloric acid absorbed by the crude product. The product is further purified by suitable recrystallization from a mixture of acetone and benzene (1:2). 51.5 g (72% yield) of a white crystalline solid, m.p. 157°-159° C, are obtained.

Analysis: Calculated for : $C_8H_6O_6F_3P$: 33.59% C; 2.11% H; 33.55% O; 19.92% F; 10.83 P. Found: 33.47 - 33.51% C; 2.10 - 2.14% H; 33.23 - 33.58% O; 20.07 - 19.85% F; 10.71 - 10.89% P.

Qualitative assays for free phenolic groups and for chlorine ions were negative.

EXPERIMENTAL AND CLINICAL PHARMACOLOGY

Effect on Platelet Aggregation

The effect of adenosine diphosphate (ADP) (1) (2), collagen (3) or epinephrine (4) on platelet aggregation (5) (6) is recognized as an initiator of intravascular thrombosis (7). Compare MARCUS, AJ. The Physiology of Blood Platelets. London. Grune and Stratton ed. 1965; GAARDNER, A. Nature 202; 909, 1965; HUGUES, J. C.R. Soc. Biol. (Paris) 154: 866, 1960; MILLS, DCB. J. Physiol. London. 193: 443, 1967; GAARDNER, A. Nature 192: 531, 1961; FENICHEL, RL. Biochem. Pharmacol. 23: 3273, 1974; HASLAM, RJ. Nature, 202: 765, 1964; BORN and CROSS. J. Physiol. Lond. 168: 178, 1963.

The claimed compounds have proved to be strong inhibitors of in vitro platelet aggregation induced by any of these aggregating agents: ADP, collagen and epinephrine.

Platelet aggregation was measured according to the method of Born and Cross (8) by using rat and human plasma. The results are summarized below in Tables I and II.

TABLE I

| Aggregating agent (plasma) concentration) | 2-hydroxy derivative | | 2-acetoxy derivative | | 2-phosphonoxy derivative | |
|---|---|---|---|---|---|---|
| | PC (molar)* | PAI (%) | PC (molar)* | PAI (%) | PC (molar)* | PAI (%) |
| | $0.83 \times 10^{-3}$ | — | $0.83 \times 10^{-3}$ | 26.0 | $0.83 \times 10^{-3}$ | 11.2 |
| ADP | $2.08 \times 10^{-3}$ | — | $2.08 \times 10^{-3}$ | 37.5 | $2.08 \times 10^{-3}$ | 23.1 |
| $4.1 \times 10^{-6}$M | $4.15 \times 10^{-3}$ | — | $4.15 \times 10^{-3}$ | 51.9 | $4.15 \times 10^{-3}$ | 57.5 |
| | $6.25 \times 10^{-3}$ | 60.2 | $6.25 \times 10^{-3}$ | — | $6.25 \times 10^{-3}$ | — |
| | $8.30 \times 10^{-3}$ | 89.2 | $8.30 \times 10^{-3}$ | 93.7 | $8.30 \times 10^{-3}$ | 69.8 |
| Epinephrine** | — | — | — | — | — | — |
| Collagen | $4.15 \times 10^{-3}$ | 27.2 | $4.15 \times 10^{-3}$ | 34.5 | $4.15 \times 10^{-3}$ | 45.5 |
| 33.3 μg/ml | $8.30 \times 10^{-3}$ | 48.3 | $8.30 \times 10^{-3}$ | 52.7 | $8.30 \times 10^{-3}$ | 94.5 |

IN VITRO INHIBITORY EFFECT OF THREE 4-TRIFLUOROMETHYLBENZOIC ACID DERIVATIVES ON RAT PLATELET AGGREGATION INDUCED BY ADP, EPINEPHRINE AND COLLAGEN.
Key : PC = Plasma Concentration; PAI = Platelet Aggregation Inhibition

*The percent of inhibition with respect to control was calculated using the method described by McKenzie (Proc. Soc. Exp. Biol. Med. 137: 662, 1971).

**Experiments with epinephrine in rats were omitted, because, in accordance with other authors, we have found that epinephrine has no influence on rat platelets (Calkins, J. J. Med. 5: 292: 1974).

TABLE II

| Aggregating agent and concentration thereof in plasma | 2-hydroxy derivative | | 2-acetoxy derivative | | 2-phosphonoxy derivative | |
|---|---|---|---|---|---|---|
| | PC (molar) | PAI (%)* | PC (molar) | PAI (%)* | PC (molar) | PAI (%)* |
| ADP | $6.25 \times 10^{-3}$ | 70.0 | $6.25 \times 10^{-3}$ | 22.5 | $6.25 \times 10^{-3}$ | 56.6 |
| $1.6 \times 10^{-6}$M | $8.30 \times 10^{-3}$ | 100.0 | $8.30 \times 10^{-3}$ | 38.6 | $8.30 \times 10^{-3}$ | 60.8 |
| | $3.30 \times 10^{-3}$ | 32.0 | — | — | — | — |
| Epinephrine | $8.10 \times 10^{-3}$ | 91.0 | — | — | — | — |
| $1.4 \times 10^{-6}$M | — | — | $17.0 \times 10^{-3}$ | 74.0 | $17.0 \times 10^{-3}$ | 59.0 |
| | — | — | $4.10 \cdot 10^{-3}$ | 37.5 | $4.10 \times 10^{-3}$ | 0.0 |
| Collagen | $8.30 \times 10^{-3}$ | 58.0 | $8.30 \times 10^{-3}$ | 62.0 | $8.30 \times 10^{-3}$ | 12.6 |
| 33.3 mcg/ml | $17.0 \times 10^{-3}$ | 75.0 | — | — | — | — |

IN VITRO INHIBITORY ACTION OF THREE 4-TRIFLUOROMETHYLBENZOIC ACID DERIVATIVES ON HUMAN PLATELET AGGREGATION INDUCED BY ADP, EPINEPHRINE AND COLLAGEN.
Key : PC = Plasma Concentration: PAI = Platelet Aggregation Inhibition

*The percent of inhibition was calculated using the method described by McKenzie (Proc. Soc. Exp. Biol. Med. 137: 662, 1971).

These in vitro tests show that the three compounds have a clear inhibitory effect on rat and human platelet aggregation, differences among them being not significant.

In view of these results and prior to undertaking any in vivo tests, acute toxicity and gastric tolerance tests on rats were carried out. 2-hydroxy-4-trifluoromethylbenzoic acid produced a high incidence of serious gastrointestinal disturbances, including bleeding of the gastric mucosa and peptic ulcers, due to the presence of a free phenolic group on the molecule. For this reason this compound has not been included in further in vivo experimentation. However, the other two compounds were well tolerated and satisfactory low acute toxicity values were found (approximately 500 mg/kg for both substances).

In the in vivo tests on humans, the two selected compounds were administered per os during six consecutive days at equimolar doses: 200 mg three times a day of 2-acetoxy-4-trifluoromethylbenzoic acid and 248 mg three times a day of 2-phosphonoxy-4-trifluoromethylbenzoic acid.

Blood was collected on the first, fourth and seventh day of the test and the platelet aggregation induced by ADP, epinephrine and collagen was determined according to the above-mentioned Born method. The results are summarized in Tables III and IV.

therapeutical use. Compare: MOSER, KM, Antithrombotic and Thrombolytic drugs, in Rubin AA ed. Search for New Drugs. Markel Dekker Inc. New York 1972 p. 317; FLEMING, JS, Antithrombotic agents, in Heinzelman RV, Annual Reports in Medicinal Chemistry Vol. 9, Academic Press, New York, 1974, p. 75; and BREDDIN, K, Prophylaxis of Arterial and Venous Thrombosis by Inhibitors of Platelet Aggregation, Thrombosis 59 (supp.): 239, 1974.

Besides, one of the factors which determines whether a thrombus will propagate is the degree of blood fibrinolytic activity. Increasing the fibrinolytic activity is therefore a desirable objective in the field of thromboembolic therapy. See THOMAS, DP, The Clinical use of Anti-Thrombotic drugs. Rationale and Results, in Medicinal Chemistry IV, Proceedings of the 4th International Symposium on Medicinal Chemistry, Noord-

TABLE III

| | | ADP ($\mu M$) | | | EPINEPHRINE ($\mu M$) | | |
|---|---|---|---|---|---|---|---|
| | HUMANS | Control | 4th day | 7th day | Control | 4th day | 7th day |
| 2-acetoxy-4- | 1 (C.S.) | 0.50 | — | 2.50 | 0.25 | — | 1.25 |
| trifluoromethyl | 2 (A.S.) | 0.50 | 2.50 | 1.25 | 0.25 | 0.25 | 0.25 |
| benzoic acid | 3 (T.D.) | 0.50 | 2.50 | 2.50 | 1.25 | 1.25 | 12.5 |
| | 4 (J.M.) | >1.25 | >2.50 | 2.50 | 1.25 | 12.5 | 1.25 |
| | 5 (A.M.) | 2.50 | >2.50 | 2.50 | 1.25 | 1.25 | 1.25 |
| 2-phosphonoxy-4- | 1 (J.J.P.) | 2.50 | 2.50 | 1.25 | 12.5 | 1.25 | 1.25 |
| trifluoromethyl | 2 (M.V.) | 2.50 | 1.25 | 1.25 | 1.25 | 1.25 | 0.25 |
| benzoic acid | 3 (C.T.) | 2.50 | 2.50 | 1.25 | >125 | 12.5 | 1.25 |
| | 4 (R.P.) | 1.25 | 1.25 | 1.25 | 1.25 | 0.25 | 0.25 |
| | 5 (A.A.) | 1.25 | 2.50 | 1.25 | 1.25 | 1.25 | 1.25 |
| | 6 (M.P.) | 2.50 | >2.50 | 1.25 | 1.25 | 125 | 12.5 |

EFFECT OF 2-ACETOXY-4-TRIFLUOROMETHYLBENZOIC ACID
AND 2-PHOSPHONOXY-4-TRIFLUOROMETHYLBENZOIC
ACID ON PLATELET AGGREGATION INDUCED BY ADP AND
EPINEPHRINE AFTER ORAL ADMINISTRATION TO HUMANS*

*The figures express the concentration ($\mu M$) that produces irreversible platelet aggregation.

TABLE IV

| | | COLLAGEN (33.3 $\mu g/m$) | | | | | | | | |
|---|---|---|---|---|---|---|---|---|---|---|
| | | CONTROL | | | 4TH DAY | | | 7TH DAY | | |
| | HUMANS | delay (xc) | x (mm) | y (mm) | delay (xc) | x (mm) | y (mm) | delay (xc) | x (mm) | y (mm) |
| 2-acetoxy-4- | 1 (C.S.) | 36 | 19 | 73 | — | — | — | 108 | 36 | 24 |
| trifluoromethyl | 2 (A.S.) | 30 | 22 | 51 | 60 | 22 | 41 | 60 | 13 | 58 |
| benzoic acid | 3 (T.D.) | 48 | 13 | 33 | 72 | 24 | 41 | 96 | 31 | 46 |
| | 4 (J.M.) | 24 | 22 | 63 | 60 | 17 | 41 | 72 | 16 | 37 |
| | 5 (A.M.) | 36 | 61 | 54 | 72 | 25 | 45 | 84 | 22 | 38 |
| 2-phosphonoxy-4- | 1 (J.J.P.) | 48 | 23 | 44 | 36 | 14 | 49 | 48 | 13 | 53 |
| trifluoromethyl | 2 (M.V.) | 36 | 18 | 50 | 24 | 16 | 42 | 24 | 14 | 38 |
| benzoic acid | 3 (C.T.) | 60 | 20 | 45 | 48 | 17 | 36 | 48 | 15 | 36 |
| | 4 (R.P.) | 24 | 22 | 50 | 24 | 22 | 36 | 36 | 23 | 26 |
| | 5 (A.A.) | 24 | 20 | 66 | 36 | 18 | 37 | 36 | 12 | 48 |
| | 6 (M.P.) | 84 | 27 | 35 | 48 | 17 | 41 | 36 | 13 | 48 |

EFFECT OF 2-ACETOXY-4-TRIFLUOROMETHYLBENZOIC ACID
AND 2-PHOSPHONOXY-4-TRIFLUOROMETHYLBENZOIC
ACID ON PLATELET AGGREGATION INDUCED BY
COLLAGEN AFTER ORAL ADMINISTRATION TO HUMANS*.

*An increase of delay time and x and a decrease of y with respect to control indicate an inhibitory effect on platelet aggregation (see FIG. 1).

The results indicated in the Tables show that the phosphono derivative of 2-hydroxy-4-trifluoromethylbenzoic acid has only a slight in vivo action on human platelet aggregation, while the acetyl derivative is a far more effective compound.

Effect on Blood Coagulation and Fibrinolysis

Blood coagulation modifications also appear to play an important role in the genesis of thrombotic diseases. Actually anticoagulants have been in use for many decades and a majority of clinical studies have shown that oral anticoagulants reduce the incidence of thrombosis and of thromboembolic complications. This anticoagulant therapy has involved the use of highly toxic or hazardous substances (heparin, coumarin, snake venoms, etc.) with little probability of a safe long-lasting wijkerhout 1974, Elsevier Scientific Publishing Co. Amsterdam, p. 173.

The potential anticoagulant and fibrinolytic activity of the claimed compounds has therefore likewise been investigated. For this purpose, with the same blood samples used for the determination of in vivo antiaggregating action on humans, the following parameters were examined: clotting time, bleeding time (Duke test), tourniquet test, Parrot's test, plasma prothrombine test (Quick test), activated partial thromboplastin test (APTT), activated Kaolin test, Howell's test, serum prothrombin time, euglobulin lysis time, Von Kaula's test, degradation products of fibrinogen (DPF), platelet count, clot retraction, hematocrit and thromboelastogram. The results are indicated in Table V.

The interpretation of these results indicates that both, the acetyl and the phosphono derivatives of 2-hydroxy-4-trifluoromethyl benzoic acid exert an anticoagulant action and produce an increase of the blood fibrinolytic activity, differences being in favor of the acetyl derivative.

(a) With 2-hydroxy-4-trifluoromethylbenzoic acid

Due to the mentioned irritating action of the compound on the gastric mucosa, in formulating pharmaceutical preparations, care must be taken to avoid direct contact with the upper digestive tract mucosa. Thus, enteric formulations (soluble only in the intestine) or pH adjusted formulations must be employed.

TABLE V

| | COAGULATION AND FIBRINOLYSIS TESTS | 2-acetoxy-4-trifluoromethyl benzoic acid | | | 2 phosphonoxy-4-trifluoromethyl benzoic acid | | |
|---|---|---|---|---|---|---|---|
| | | Control (0 day) | 4th day | 7th day | Control (0 day) | 4th day | 7th day |
| 1. | Clothing time (sec) | 443.3±13.0 | 521.6±29.7 | 526.6±25.6 | 427.0±19.6 | 527.5±30.8 | 520.0±28.6 |
| 2. | Bleeding time (sec) Duke test | 121.0±11.3 | 133.0±19.3 | 116.0±13.8 | 177.5±32.0 | 155.0±19.6 | 112.5±10.8 |
| 3. | Tourniquet test | | NEGATIVE | | | NEGATIVE | |
| 4. | Parrot's test | POSITIVE IN TWO HUMANS | | | POSITIVE IN FOUR HUMANS | | |
| 5. | Plasma prothrombine test: Quick test | 0.921±0.03 | 0.938±0.02 | 0.933±0.02 | 1.03±0.02 | 0.966±0.02 | 0.986±0.02 |
| 6. | Activated partial thromboplastin test: APTI | 0.868±0.03 | 0.720±0.03 | 0.890±0.03 | 0.958±0.03 | 0.823±0.04 | 0.960±0.01 |
| 7. | Activated kaolin test | 0.864±0.03 | 0.797±0.03 | 0.890±0.02 | 0.993±0.02 | 0.768±0.05 | 0.960±0.04 |
| 8. | Howell's test | 0.906±0.03 | 0.723±0.04 | 0.807±0.04 | 0.883±0.05 | 0.873±0.04 | 0.793±0.07 |
| 9. | Serum prothrombin time (sec) | 52.5±6.5 | 38.8±2.7 | 37.3±3.9 | 32.8±3.9 | 34.8±2.6 | 33.0±1.5 |
| 10. | Euglobin lysis time (min): Von Kaulas's test | 178.3±19.0 | 140.0±12.3 | 136.1±11.5 | 196.6±19.6 | 145.1±9.3 | 136.6±9.0 |
| 11. | Degradation products of fibrinogen: DPF | | NEGATIVE | | | NEGATIVE | |
| 12. | Platelet count (per $mm^3$)×$10^3$ | 252.2±12.6 | 236.6±12.8 | 231.1±11.6 | 235.0±19.3 | 253.3±10.5 | 223.3±12.8 |
| 13 | Clot retraction | | NEGATIVE | | | NEGATIVE | |
| 14. | Hematocrit | 44.4±1.4 | 44.0±1.2 | 44.8±1.3 | 42.9±0.5 | 42.0±1.0 | 45.0±1.4 |
| 15. | Thromboelastogram $r$ (cm) | 15.5±1.6 | 19.6±1.2 | 21.6±3.6 | 18.2±1.0 | 17.8±2.0 | 15.0±1.3 |
| | **K (cm) | 22.1±2.3 | 24.6±1.6 | 22.1±1.5 | 28.2±2.6 | 25.3±2.7 | 19.9±1.9 |

EFFECT OF 2-ACETOXY-4-TRIFLUOROMETHYLBENZOIC ACID AND 2-PHOSPHONOXY-4-TRIFLUOROMETHYLBENZOIC ACID ON BLOOD COAGULATION FACTORS AND FIBRINOLYSIS*.

*This Table shows the mean values (±s.e.m.) obtained on 9 humans treated with 2-acetoxy-4-trifluoromethylbenzoic acid and on 6 humans treated with 2-phosphonoxy-4-trifluoromethylbenzoic acid. An increase of the mean values (±s.e.m.) of parameters 1 and 2 or a decrease of parameters 5,6,7,8,9,10 and 11 with respect to control, mean an inhibitory effec of drugs on the blood coagulation and fibrinolysis.

Figure 2:
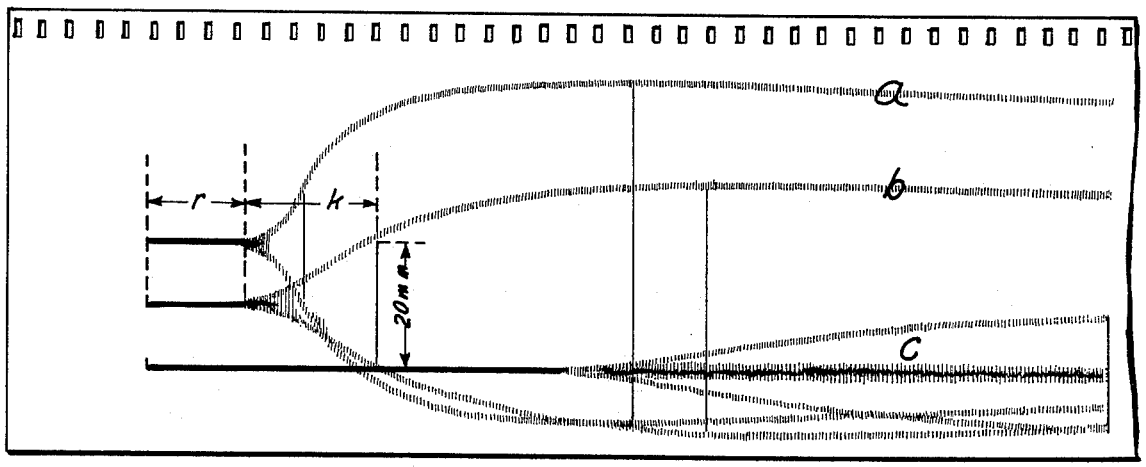
FIG. 2 shows typical human thromboelastograms of rich platelet plasma ($a$), blood ($b$) and poor platelet plasma ($c$). The values $r$ and $k$ (in parameter 15 of Table V) correspond to blood ($b$). Their significance appears from the Figure.

**An increase of r and k values with respect to control, indicates an inhibitory effect of the drugs on blood coagulation and also on platelet aggregation. These figures are indicated in FIG. 2 which corresponds to a normal thromboelastogram.

It is known that many compounds possess potent in vitro activity, but sometimes fail to be effective in vivo, due to poor absorption, rapid metabolism or the presence of undesirable side effects. The three tested compounds have a clear in vitro activity, but considering their relative in vivo activity and side effects, the 2-acetoxy derivative of 4-trifluoromethylbenzoic acid appears to be the most desirable for therapeutical use.

However, specific pharmacotechnical steps could obviate the shortcomings initially observed for a particular substance or preparation of the same, for example: enteric coating, pH adjustment by means of salification, micronisation of the particles, etc. Thus, every compound should receive a different pharmacotechnical manipulation in order to obtain the highest effectiveness and the smallest incidence of side effects. Besides, since all three compounds are solid and have similar physical properties, the pharmaceutical compositions described below may be equally suitable in the case of any of the three compounds.

In all instances conventional excipients, sweetening, flavoring or antiseptic agents (when necessary) can be used, as illustrated in the following examples:

A. ORAL PREPARATIONS

The usual unit dosage in the case of a solid preparation is 100 mg. to 400 mg. and, preferably, 200 mg. to 300 mg. Similarly, in case of a syrup, the usual unit dosage is 100 mg. to 400 mg. and, preferably, 200 mg. to 300 mg.

EXAMPLE 6

Enteric capsules:

| | |
|---|---|
| 2-hydroxy-4-trifluoromethylbenzoic acid | 200 mg |
| Magnesium stearate, q. s. | 1 capsule* |

*Enteric capsules employed are resistant to gastric juice for 2 hours at 37° C.

EXAMPLE 7

Enteric tablets:

| | | |
|---|---|---|
| 2-hydroxy-4-trifluoromethylbenzoic acid | | 200 mg |
| Starch | | |
| Aerosil (colloidal amorphous silicon dioxide) | q.s. | |
| Magnesium stearate | | 1 tablet |

After compression, tablets are coated with a first layer of syrup, collodion and carbowax (a mixture of polyethylene glycols having an average molecular weight above 1000) and then further with a layer of Eudragit L (anionic polymers of methacrylic acid and esters of the same).

EXAMPLE 8

Syrup:

| | |
|---|---|
| 2-hydroxy-4-trifluoromethylbenzoic acid, sodium salt (equivalent to 4.00 g of the free acid) | 4.43 g |
| Sugar | 40.00 g |

| | | |
|---|---|---|
| Saccharin | | 80.00 g |
| Nipagin (P-hydroxybenzoic acid methyl ester), antiseptic | | |
| Coloring agent | q.s. | 100.00 ml |
| Flavor correctives | | |
| Water | | |

(b) With 2-acetoxy-4-trifluoromethylbenzoic acid

EXAMPLE 9

Gelatin capsules:

| | |
|---|---|
| 2-acetoxy-4-trifluoromethylbenzoic acid | 200 mg |
| Lactose, q.s. | 1 capsule |

EXAMPLE 10

Tablets or dragees:

| | |
|---|---|
| 2-acetoxy-4-trifluoromethylbenzoic acid | 200 mg. |
| Magnesium stearate, q.s. | 1 tablet or dragee |

(c) With 2-phosphono-4-trifluoromethylbenzoic acid

The dosage is increased with this compound in order to compensate for the latter activity.

EXAMPLE 11

Gelatin capsules:

| | |
|---|---|
| 2-phosphono-4-trifluoromethylbenzoic acid | 300 mg |
| Lactose, q.s. | 1 capsule |

EXAMPLE 12

Tablets or dragees:

| | | |
|---|---|---|
| 2-phosphono-4-trifluoromethylbenzoic acid | | 300 mg |
| Starch | | |
| Magnesium stearate | q.s. | 1 tablet or dragee |
| Aerosil (colloidal amorphous silicon dioxide) | | |

EXAMPLE 13

Sachets:

| | |
|---|---|
| 2-phosphono-4-trifluoromethylbenzoic acid | 300 mg |
| Arginine (as pH corrective) | |
| Mannitol | |
| Sugar | |

| | | |
|---|---|---|
| Saccharin | | 1 sachet |
| Flavor correctives | q.s. | |
| Coloring agent | | |

B. RECTAL PREPARATIONS (a) With 2-acetoxy-4-trifluoromethylbenzoic acid

Due to poorer rectal absorption, the particle size is particularly important. Previous micronization of the effective agent enhances the absorption.

EXAMPLE 14

Suppositories:

| | |
|---|---|
| Micronized 2-acetoxy-4-trifluoromethylbenzoic acid | 250 mg |
| Supocire BM (a mixture of mono-, di- and triglycerides of saturated fatty acids) q.s. | 1 suppository |

Ten mg of lidocaine per suppository may be added in order to avoid local intolerances.

In a general way, the mean daily dosage for adults is 1–6 unit doses (capsules, tablets, dragees, sachets or suppositories) or 1–6 5 ml spoonsful of syrup.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method for the treatment and prophylaxis of cardiovascular conditions due to an abnormal platelet aggregation, coagulation and fibrinolysis comprising administering to a patient by oral administration a compound of the formula

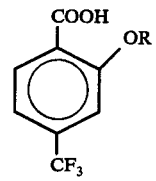

wherein R is hydrogen or lower alkanoyl as active agent, together with a carrier therefor, at a dosage of about 1 to 6 unit doses of about 200 to 300 mg each of said active agent or about 1 to 6 units at about 5 ml each of the active agent when in the form of a syrup.

2. The method of claim 1 wherein the said active agent is 2-acetoxy-4-trifluoromethylbenzoic acid.

* * * * *